United States Patent [19]

(12) United States Patent
Carter

(10) Patent No.: US 8,481,488 B2
(45) Date of Patent: Jul. 9, 2013

(54) COMPOSITIONS AND METHODS FOR REDUCING THE RISK OF PRETERM LABOR

(75) Inventor: Darryl Carter, Owings Mills, MD (US)

(73) Assignee: Nora Therapeutics Inc., Palo Alto, CA (US)

( * ) Notice: Subject to any disclaimer, the term of this patent is extended or adjusted under 35 U.S.C. 154(b) by 0 days.

(21) Appl. No.: 13/458,823

(22) Filed: Apr. 27, 2012

(65) Prior Publication Data
US 2012/0269763 A1 Oct. 25, 2012

Related U.S. Application Data

(60) Continuation of application No. 12/714,824, filed on Mar. 1, 2010, now abandoned, which is a continuation of application No. 12/116,401, filed on May 7, 2008, now Pat. No. 7,744,864, which is a division of application No. 11/411,361, filed on Apr. 24, 2006, now Pat. No. 7,470,662, which is a continuation of application No. PCT/US2004/035468, filed on Oct. 25, 2004.

(60) Provisional application No. 60/514,472, filed on Oct. 24, 2003.

(51) Int. Cl.
*A61K 38/00* (2006.01)
*A61K 45/00* (2006.01)

(52) U.S. Cl.
USPC .................. 514/9.8; 424/85.1; 530/351

(58) Field of Classification Search
None
See application file for complete search history.

(56) References Cited

U.S. PATENT DOCUMENTS

| | | |
|---|---|---|
| 4,554,101 A | 11/1985 | Hopp |
| 5,104,651 A | 4/1992 | Boone et al. |
| 5,147,799 A | 9/1992 | Bursuker et al. |
| 5,276,017 A | 1/1994 | Feinberg et al. |
| 5,284,656 A | 2/1994 | Platz et al. |
| 5,320,840 A | 6/1994 | Camble et al. |
| 5,399,345 A | 3/1995 | Schumacher et al. |
| 5,416,195 A | 5/1995 | Camble et al. |
| 5,422,248 A | 6/1995 | Smith et al. |
| 5,766,944 A | 6/1998 | Ruiz |
| 5,837,230 A | 11/1998 | Nakai et al. |
| 5,888,495 A | 3/1999 | Schrier et al. |
| 5,891,429 A | 4/1999 | Clark et al. |
| 5,895,646 A | 4/1999 | Wang |
| 5,908,763 A | 6/1999 | Clark et al. |
| 5,919,757 A | 7/1999 | Michaelis et al. |
| 5,981,551 A | 11/1999 | Luengo et al. |
| 5,989,537 A | 11/1999 | Holly et al. |
| 6,040,340 A | 3/2000 | Chwalisz et al. |
| 6,150,085 A | 11/2000 | Hess et al. |
| 6,162,417 A | 12/2000 | Goodman et al. |
| 6,162,427 A | 12/2000 | Baumann et al. |
| 6,166,183 A | 12/2000 | Ishikawa et al. |
| 6,261,550 B1 | 7/2001 | Osslund |
| 6,277,379 B1 | 8/2001 | Oaks et al. |
| 6,565,841 B1 | 5/2003 | Niven et al. |
| 6,646,110 B2 | 11/2003 | Nissen et al. |
| 6,946,548 B2 | 9/2005 | Sarkar et al. |
| 6,979,674 B1 | 12/2005 | Goldenberg et al. |
| 7,470,662 B2 | 12/2008 | Carter |
| 7,615,531 B2 | 11/2009 | Carter |
| 7,700,548 B2 | 4/2010 | Carter |
| 7,744,864 B2 | 6/2010 | Carter |
| 7,824,712 B2 | 11/2010 | Carter |
| 7,939,491 B2 | 5/2011 | Carter |
| 2001/0009922 A1 | 7/2001 | Faller |
| 2002/0086296 A1 | 7/2002 | Meyers |
| 2003/0068664 A1 | 4/2003 | Albitar et al. |
| 2003/0166527 A1 | 9/2003 | Sarkar et al. |
| 2004/0105858 A1 | 6/2004 | Kim et al. |
| 2004/0137557 A1 | 7/2004 | DeFrees et al. |
| 2004/0224393 A1 | 11/2004 | Kwon et al. |
| 2009/0035262 A1 | 2/2009 | Carter |
| 2010/0158972 A1 | 6/2010 | Carter |
| 2012/0315243 A1 | 12/2012 | Carter |

FOREIGN PATENT DOCUMENTS

| | | |
|---|---|---|
| WO | 2005/039505 | 5/2005 |
| WO | 2006/128176 | 11/2006 |
| WO | 2008/009705 | 1/2008 |

OTHER PUBLICATIONS

Arpaci et al., "A Successful and Simplified Filgrastim Primed Single Apheresis Method Without Large Volume Apheresis for Peripheral Blood Stem Cell Collection," *Jpn. J. Clin. Oncol.* 30(3): 153-158, 2000.
Berenson et al., "Transplantation of CD34+ Hematopoietic Progenitor Cells," *Cancer Investigation* 14(6): 589-596, 1996.
Boxer et al., "Outcomes of Pregnancies for Women with Severe Chronic Neutropenia with or without G-CSF Treatment," Paper #1490 from 53$^{rd}$ ASH Annual Meeting and Exposition, Dec. 10-13, 2011, URL=//ash.confex.com/ash/2010/webprogram/Paper33438.html, download date Jul. 3, 2012, 2 pages.
Bueno et al., "Endoscopic placement of direct percutaneous jejunostomy tubes in patients with complications after esophagectomy," *Gastrointestinal Endoscopy* 57(4): 536-540, 2003.

(Continued)

*Primary Examiner* — Gyan Chandra
(74) *Attorney, Agent, or Firm* — Seed IP Law Group PLLC

(57) ABSTRACT

The present invention provides compositions, kits and methods for the prevention of spontaneous abortion or implantation failure during assisted reproduction. The compositions, kits and methods provide an effective amount of granulocyte colony stimulating factor to prevent spontaneous abortion or implantation failure of an embryo. The present invention also provides compositions, kits and methods for the treatment or prevention of preeclampsia and preterm labor.

54 Claims, No Drawings

OTHER PUBLICATIONS

Calhoun et al., "Transplacental passage of recombinant human granulocyte colony-stimulating factor in women with an imminent preterm delivery," *Am. J. Obstet. Gynecol. 174*(4): 1306-1311, Apr. 1996.

Calhoun et al., "A randomized pilot trial of administration of granulocyte colony-stimulating factor to women before preterm delivery," *American Journal of Obstetrics & Gynecology 179*: 766-771, 1998.

Cameo et al., "Similar embryotoxic effects of sera from infertile patients and exogenous interferon-γ on long-term in-vitro development of mouse embryos," *Human Reproduction 14*(4): 959-963, 1999.

Cavallaro et al., "Three to six year follow-up of normal donors who received recombinant human granulocyte colony-stimulating factor," *Bone Marrow Trans. 25*: 85-89, 2000.

Chaouat et al., "Implantation: can immunological parameters of implantation failure be of interest for preeclampsia?," *Journal of Reproductive Immunology 59*: 205-217, 2003.

Clark et al., "Prevention of spontaneous abortion in DBA/2-mated CBA/J mice by GM-CSF involves CD8+ T cell-independent suppression of natural effector cell cytotoxicity against trophoblast target cells," *Cellular Immunology 154*: 143-152, 1994.

Clark et al., "Unexplained sporadic and recurrent miscarriage in the new millennium: a critical analysis of immune mechanisms and treatments," *Human Reproduction Update 7*: 501-511, 2001.

Delagrave et al., "Recursive ensemble mutagenesis," *Protein Engineering 6*(3): 327-331, 1993.

Deng et al., "Site-Directed Mutagenesis of Virtually Any Plasmid by Eliminating a Unique Site," *Analytical Biochemistry 200*: 81-88, 1992.

Doncarli et al., "Conversion in vivo from an early dominant Th0/Th1 response to a Th2 phenotype during the development of collagen-induced arthritis," *Eur. J. Immunol. 27*: 1451-1458, 1997.

Dreger et al., "G-CSF-mobilized peripheral blood progenitor cells for allogenic transplantation: safety, kinetics of mobilization, and composition of the graft," *British Journal of Haematology 87*: 609-613, 1994.

Duan et al., "Production of granulocyte colony stimulating factor in decidual tissue and its significance in pregnancy," *Osaka City Med. J. 36*: 81-97, 1990.

Dudrick et al., "Total Parenteral Nutrition: Techniques, Complications, and Prevention," *Surgical Technology International 7*: 174-184, 1998.

Fukunaga et al., "Purification and Characterization of the Receptor for Murine Granulocyte Colony-stimulating Factor," *The Journal of Biological Chemistry 266*(23): 14008-14015, Aug. 15, 1990.

Griebel et al., "Management of Spontaneous Abortion," *American Family Physician 72*(7): 1243-1250, Oct. 1, 2005.

Huang et al., "Maintaining hyporesponsiveness and polarization potential of T cells after in vitro mixture of G-CSF mobilized peripheral blood grafts and G-CSF primed bone marrow grafts in different proportions," *Transplant Immunology 17*: 193-197, 2007.

Kaufmann et al., "Term delivery in a woman with severe congenital neutropenia, treated with growth colony stimulating factor," *Human Reproduction 13*(2): 498-499, 1998.

Kocherlakota et al., "Preliminary Report: rhG-CSF May Reduce the Incidence of Neonatal Sepsis in Prolonged Preeclampsia-associated Neutropenia," *Pediatrics 102*: 1107-1111, 1998.

Kozak, "At Least Six Nucleotides Preceding the AUG Initiator Codon Enhance Translation in Mammalian Cells," *J. Mol. Biol. 196*: 947-950, 1987.

Krishnan et al., "T Helper 1 Response Against *Leishmania major* in Pregnant C57BL/6 Mice Increases Implantation Failure and Fetal Resorptions," *The Journal of Immunology 156*: 653-662, 1996.

Kwak-Kim et al., "Increased T helper 1 cytokine responses by circulating T cells are present in women with recurrent pregnancy losses and in infertile women with multiple implantation failures after IVF," *Human Reproduction 18*(4): 767-773, 2003.

Lecoeur et al., "Strategies for phenotyping apoptotic peripheral human lymphocytes comparing ISNT, annexin-V and 7-AAD cytofluorometric staining methods," *Journal of Immunological Methods 209*: 111-123, 1997.

Link et al., "CD34 Positive Blood Cells For Allogeneic Progenitor and Stem Cell Transplantation," *Leukemia and Lymphoma 26*: 451-465, 1997 [current as of Jul. 22, 2008].

Matsubara et al., "Concentrations of Serum Granulocyte-Colony-Stimulating Factor in Normal Pregnancy and Preeclampsia," *Hypertension in Pregnancy 18*: 95-106, 1999.

Mauri et al., "Relationship between Th1/Th2 cytokine patterns and the arthritogenic response in collagen-induced arthritis," *Eur. J. Immunol. 26*: 1511-1518, 1996.

Medlock et al., "Granulocyte colony-stimulating factor crosses the placenta and stimulates fetal rat granulopoiesis," *Blood 81*(4): 916-922, 1993.

Merck Manual 17$^{th}$ edition, Merck Research Laboratories, Whitehouse Station, New Jersey, Chapter 252, pp. 2053-2061, 1999.

Merck Manual 17$^{th}$ edition, Merck Research Laboratories, Whitehouse Station, New Jersey, p. 1995 (1999).

Mohandas et al., "Total parenteral nutrition," *The National Medical Journal of India 16*(1): 29-33, 2003.

Mori et al , "Immunomolecular mechanisms in mammalian Implantation," *Endocrine Journal 41*(Supp): s17-s31, 1994.

Morris et al., "Stem cell mobilization with G-CSF analogs: a rational approach to separate GVHD and GVL?," *Blood 107*(9): 3430-3435, May 1, 2006.

Moverare et al., "Study of the Th1/Th2 balance, including IL-10 production, in cultures of peripheral blood mononuclear cells from birch-pollen-allergic patients," *Allergy 55*: 171-175, 2000.

Okkels, "A URA3 promoter deletion in a pYES vector increases the expression level of preferred delivery method," *Ann. NY Acad. Sci. 782*: 202-207, 1996.

Oksenberg et al., "In Vitro Suppression of Murine Blastocysts Growth by Sera From Women With Reproductive Disorders," *American Journal of Reproductive Immunology and Microbiology 11*: 118-124, 1986.

Papadimitriou et al., "Non-Cryopreserved Peripheral Blood Progenitor Cells Collected by a Single Very Large-Volume Leukapheresis: A Simplified and Effective Procedure for Support of High-Dose Chemotherapy," *Journal of Clinical Apheresis 15*: 236-241, 2000.

Perricone et al., "GM-CSF and pregnancy: Evidence of significantly reduced blood concentrations in unexplained recurrent abortion efficiently reverted by intravenous immunoglobulin treatment," *American Journal of Reproductive Immunology 50*: 232-237, 2003.

Raghupathy et al., "Cytokine production by maternal lymphocytes during normal human pregnancy and in unexplained recurrent spontaneous abortion," *Human Reproduction 15*: 713-718, 2000.

Raghupathy et al., "Maternal Th1- and Th2-Type Reactivity to Placental Antigens in Normal Human Pregnancy and Unexplained Recurrent Spontaneous Abortions," *Cellular Immunology 196*: 122-130, 1999.

Raziuddin et al., "Divergent Cytokine Production Profile in Behçet's Disease. Altered Th1/Th2 Cell Cytokine Pattern," *The Journal of Rheumatology 25*(2): 329-333, 1998.

Reidhaar-Olson et al., "Identification of Residues Critical to the Activity of Human Granulocyte Colony-Stimulating Factor," *Biochemistry 35*: 9034-9041, 1996.

Reidhaar-Olson et al., "Random Mutagenesis of Protein Sequences Using Oligonucleotide Cassettes," *Methods in Enzymology 208*: 564-568, 1991.

Rezaei et al., "T-helper (1) cytokines increase during early pregnancy in women with a history of recurrent spontaneous abortion," *MedSciMonit 8*(8): CR607-610, 2002.

Roussev et al., "Validation of an Embryotoxicity Assay," *American Journal of Reproductive Immunology 33*: 171-175, 1995.

Saito et al., "Elevation of Amniotic Fluid Interleukin 6 (IL-6), IL-8 and Granulocyte Colony Stimulating Factor (G-CSF) in Term and Preterm Parturition," *Cytokine 5*(1): 81-88, Jan. 1993.

Sanger et al., "DNA sequencing with chain-terminating inhibitors," *Proc. Natl. Acad. Sci. USA 74*(12): 5463-5467, Dec. 1997.

Sbracia et al., "Use of GM-CSF 1 in the Treatment of Habitual Abortion: a Pilot Study," *Fertility & Sterility 70*(3, Suppl. 1): S62-S63, 1995.

Scarpellini et al., "Effectiveness of GM-CSF 1 in the Treatment of Habitual Abortion in a Controlled Study," *American Journal of Reproductive Immunology (Abstracts) 51*: 433-434, 2004.

Scarpellini et al., "Effectiveness of GM-CSF 1 in the treatment of habitual abortion in a controlled study," *Fertility and Sterility 80*(Suppl 3): S288, 2003.

Schust et al., "Correlation of Serum Cytokine and Adhesion Molecule Determinations With Pregnancy Outcome," *J. Soc. Gynecol. Invest. 3*(5): 259-261, Sep./Oct. 1996.

Shike et al., "Direct percutaneous endoscopic jejunostomies for enteral feeding," *Gastrointestinal Endoscopy 44*(5): 536-540, 1996.

Stemmer et al., "Single-step assembly of a gene and entire plasmid from large numbers of oligodeoxyribonucleotides," *Gene 164*: 49-53, 1995.

Stephenson et al., "Evaluation and Management of Recurrent Early Pregnancy Loss," *Clinical Obstetrics and Gynecology 50*(1): 132-145, Mar. 2007.

Sullivan et al., "Recurrent Fetal Aneuploidy and Recurrent Miscarriage," *Obstetrics & Gynecology 104*(4): 784-788, Oct. 2004.

Sun et al., "IFN-γ Promotes Apoptosis of the Uterus and Placenta in Pregnant Rat and Human Cytotrophoblast Cells," *Journal of Interferon & Cytokine Research 27*: 567-578, 2007.

Thomason et al., "Prevalence of Embryotoxic Factor in Sera From Women With Unexplained Recurrent Abortion," *American Journal of Reproductive Immunology 34*: 338-341, 1995.

Vogel et al., "Clinical Applications of CD34+ Peripheral Blood Progenitor Cells (PBPC)," *Stem Cells 18*: 87-92 2000.

Wells et al., "Casette mutagenesis: an efficient method for generation of multiple mutations at defined sites," *Gene 34*(2-3): 315-323, 1985.

Würfel, "Approaches to a Better Implantation," *J Assisted Reproduction and Genetics 17*(8): 473, 2000.

Xing et al., "Th1/Th2 type cytokines in hepatitis B patients treated with interferon-α," *Chinese Medical Journal 114*(9): 921-924, 2001.

Yabuki et al., "Giant Lysosomes in the Renal Proximal Tubules—A Morphological Characteristic of DBA/2 and DBA/1 Mouse Kidneys," *Exp. Anim. 52*(2): 159-163, 2003.

Younghusband et al., "Mutagenesis of conserved 5' elements and transcription of a chicken H1 histone gene," *Nucleic Acids Research 14*(2): 635-644, 1986.

Zell et al., "DNA mismatch-repair in *Escherichia coli* counteracting the hydrolytic deamination of 5-methyl-cytosine residues," *The EMBO Journal 6*(6): 1809-1815, 1987.

European Search Report (European Application No. 04796441.6 filed Oct. 25, 2004).

European Search Report (European Application No. 10155708.0, based on PCT application PCT/US04/35468, filed Oct. 5, 2004).

International Search Report (International Application No. PCT/US04/35468 filed Oct. 25, 2004).

International Search Report and Written Opinion of the International Searching Authority (International Application No. PCT/US2009/042481, filed May 1, 2009).

International Search Report dated Jan. 29, 2010 for PCT/US2009/042481 (4 pages).

International Preliminary Report on Patentability (International Application No. PCT/US04/35468 filed Oct. 25, 2004).

Written Opinion of the International Searching Authority (International Application No. PCT/US04/35468 filed Oct. 25, 2004).

Supplementary European Search Report dated Jun. 10, 2009 for EP Application No. 04796441.6 (6 pages).

International Search Report dated May 28, 2010 for PCT/US2009/062321.

Daher et al., "Tumor necrosis factor during pregnancy and at the onset of labor and spontaneous abortion," *European Journal of Obstetrics & Gynecology and Reproductive Biology 83*: 77-79, 1999.

Hill et al., "T-helper 1-Type Immunity to Trophoblast in Women With Recurrent Spontaneous Abortion," *Journal of the American Medical Association 273*(24): 1933-1936, Jun. 28, 1995.

Ogasawara et al., "Elevation of Transforming Growth Factor-β1 Is Associated with Recurrent Miscarriage," *Journal of Clinical Immunology 20*(6): 453-457, 2000.

Pampfer et al., "Role of Colony Stimulating Factor-1 (CSF-1) and Other Lympho-hematopoietic Growth Factors in Mouse Pre-implantation Development." *BioEssays: News and Reviews in Molecular, Cellular and Developmental Biology 13*(10): 535-540, Oct. 1991.

Raghupathy, "Th1-type immunity is incompatible with successful pregnancy," *Immunology Today 18*(10): 478-482, Oct. 1997.

Saito et al., "Th1/Th2 balance in preeclampsia," *Journal of Reproductive Immunology 59*(2): 161-173, Aug. 2003.

US 8,481,488 B2

COMPOSITIONS AND METHODS FOR REDUCING THE RISK OF PRETERM LABOR

CROSS-REFERENCE(S) TO RELATED APPLICATION(S)

This application is a continuation of U.S. patent application Ser. No. 12/714,824, now abandoned; which is a continuation application of U.S. patent application Ser. No. 12/116,401, now U.S. Pat. No. 7,744,864, filed May 7, 2008; which is a divisional application of U.S. patent application Ser. No. 11/411,361, now U.S. Pat. No. 7,470,662, filed Apr. 24, 2006; which is a continuation application of PCT/US04/35468, filed Oct. 25, 2004; which claims priority from U.S. Provisional Application Ser. No. 60/514,472, filed Oct. 24, 2003. The entirety of all of the aforementioned applications is incorporated herein by reference.

FIELD OF THE INVENTION

The present invention relates to methods of preventing spontaneous abortion or implantation failure during assisted reproduction and methods of treating or preventing preeclampsia and preterm labor, and other forms of reproductive failure that present an immune system aberration.

BACKGROUND OF INVENTION

Conception, pregnancy and delivery require an intricate and delicate interplay of physiology and anatomy. Implantation and placentation of the embryo are complex processes involving hormonal and anatomical changes in the mother and migration and cellular division of the embryo.

Spontaneous abortion occurs in 15% of diagnosed pregnancies in women between fifteen and forty-five years of age. Recurrent spontaneous abortions are defined as the loss of three or more consecutive pregnancies and occur in about 3-4% of these women. The risk of pregnancy loss increases from 15-20% in the first pregnancy to 40% after one spontaneous abortion.

Although the majority of pregnancies lost in the first trimester are due to fetal causes; spontaneous abortion, the loss of the product of conception prior to the 20th week of pregnancy, is a disorder of unknown etiology. It has been theorized that spontaneous abortions are a natural rejection of a fetus with abnormalities incompatible with life, however, this theory has yet to be substantiated.

Risk factors for abortion include age, weight and overall health of the woman. The prevalence of spontaneous abortion increases with increasing maternal age, although not with gravidity. The risk begins to increase rapidly at age 35 years. The risk of spontaneous abortion at age 40 is approximately twice that at age 20. As families are planned later and later in life, the frequency of spontaneous abortion will only increase without effective methods of prevention.

Accompanying the rising age of hopeful parents is the increasing use of assisted reproductive techniques such as in vitro fertilization, gamete intrafallopian tube transfer (GIFT), and the like. These techniques have their own attending risks, especially to the woman during ovarian hyperstimulation. Moreover, assisted reproduction and in vitro fertilization are costly, time consuming and have a high failure rate, resulting in pregnancy in only about 25% of cases. (see Merck Manual 17th edition, 1999, Merck Research Laboratories, Whitehouse Station, N.J., p. 1995).

Threatened abortion generally presents as cramping and bleeding for which treatment is bed rest. This conservative treatment provides palliative care for the mother but does little to alter the outcome. The use of hormones is generally contraindicated due to the risk of congenital anomalies, including malformation of the vessels of the heart of the embryo and possible genital abnormalities in female offspring.

Preeclampsia and other hypertensive disorders of pregnancy are a leading global cause of maternal and infant illness and death. Symptoms of preeclampsia include hypertension, edema and proteinuria with sudden weight gain, headaches and changes in vision. Preeclampsia can prevent the placenta from getting enough blood which can cause low birth weight and other problems for the baby. Although most women with preeclampsia still deliver healthy babies, some develop eclampsia, a serious condition that threatens the life of the mother and the fetus.

The risk of preeclampsia is higher in women carrying multiple babies, in teenage mothers and in women older than age 40. Typically, preeclampsia occurs in the late 2nd or 3rd trimesters (middle to late pregnancy) though occasionally it occurs earlier. Preeclampsia affects about 5% of all pregnancies.

Mild preeclampsia is conservatively treated with strict bed rest and vigilant monitoring of blood pressure. Progression of the disorder is treated with fluids, antihypertensives and magnesium sulfate but delivery of the fetus provides the only remedy.

In addition to the physical toll of these disorders, the loss of a desired pregnancy takes a tremendous emotional toll on hopeful and expectant parents. Loss of a pregnancy can lead to feelings of inadequacy, hopelessness and guilt which can have a devastating effect on individuals and on a marriage.

New methods and compositions are always needed to reduce risks associated with pregnancy to the health of the mother and fetus. Effective prevention of spontaneous abortion can allow women, especially women at risk, to have successful pregnancies, and effective treatment or prevention of preeclampsia can reduce or eliminate one of the common health risks of pregnancy. Prevention of implantation failure during assisted reproduction, can allow successful pregnancies, reduce the risks to the woman and save time and money. Prevention of pre term labor will enhance the likelihood of normal births.

SUMMARY OF THE INVENTION

To reduce the frequency of recurrent spontaneous abortion and the failure of implantation during assisted reproduction, the present invention provides methods, compositions and kits comprising a granulocyte colony stimulating factor (GCSF or G-CSF) in an amount effective to prevent spontaneous abortion or failed implantation of a transferred embryo. The present invention is based, in part, on the discovery that GCSF can reduce or eliminate immune system mediated aberrations that are associated with spontaneous abortion or implantation failure. Based on this discovery, the present invention also provides methods of using GCSF mobilized peripheral blood stem cells to prevent spontaneous abortion or implantation failure, and the present invention also provides methods of using GCSF to treat or prevent preeclampsia or preterm labor.

In one aspect, the present invention provides methods of preventing spontaneous abortion. The methods can be administered to any female subject at risk for spontaneous abortion. Subjects at risk can be identified according to the methods described herein or according to methods known to practitioners in the art. Typically, the subject is in the first or second trimester of pregnancy. In certain embodiments, the subject is in the first 20 weeks of pregnancy. In certain embodiments, the subject is in the first or second months of pregnancy.

To prevent or reduce the risk of spontaneous abortion, a prophylactically effective amount of GCSF is administered to the subject. The GCSF can be administered by any mode of administration known to those of skill in the art. In certain embodiments, the GCSF is administered subcutaneously. The dose of GCSF can be determined by a practitioner of skill in the art as described in detail below. In certain embodiments, a dose of 10 mcg (micrograms)/kg (body weight) up through 100-500 mg is administered daily to the subject. The dose can be continued as long as necessary to prevent spontaneous abortion according to the judgment of the practitioner of skill in the art. In certain embodiments, the dose is administered through the first trimester of pregnancy. In other embodiments, the dose is administered for four, three, two or one week. In particular embodiments, the dose is administered for five, four, three, two or one day.

In another aspect, the present invention provides a method for preventing spontaneous abortion by administering to a subject mobilized peripheral blood stem cells. In this aspect, GCSF is administered to a first female subject. Preferably, the subject is not pregnant. The GCSF can optionally be administered along with chemotherapeutic or immunosuppressive therapy. Following administration of GCSF, granulocytes are collected from the patient. These granulocytes are optionally stored, typically by cryopreservation, for later administration. Preferably, the granulocytes comprise peripheral blood stem cells, and in particular, CD34+ peripheral blood stem cells.

In this aspect of the invention, the stem cells, which can be histocompatible, are administered to a pregnant subject. In particularly preferred embodiments, the administration is autologous, that is, the recipient subject is the same as the first female donor subject from whom the blood mononuclear cells were collected. However, the administration can also be allogeneic, that is, the recipient subject is not the same as the first female donor subject. An amount of the blood mononuclear cells effective to prevent spontaneous abortion is administered to the subject according to methods known to the practitioner of skill in the art.

In another aspect, the present invention provides methods of preventing implantation failure during assisted reproduction. The methods can be administered to any female subject at risk for implantation failure. Subjects at risk can be identified according to the methods described herein or according to methods known to the practitioner of skill in the art. In certain embodiments, the assisted reproduction is in vitro fertilization and transfer of an embryo.

In order to prevent implantation failure, a prophylactically effective amount of GCSF is administered to the subject. The GCSF can be administered by any mode of administration known to those of skill in the art. In certain embodiments, the GCSF is administered subcutaneously. The dose of GCSF can be determined by a practitioner of skill in the art as described in detail below. In certain embodiments, a dose of 10 mcg/kg up through 500 mg is administered daily to the subject. The dose can be continued as long as necessary to prevent implantation failure according to the judgment of the practitioner of skill in the art. In certain embodiments, the dose is administered through the first trimester of pregnancy. In other embodiments, the dose is administered for four, three, two or one week. In particular embodiments, the dose is administered for five, four, three, two or one day.

In another aspect, the present invention provides methods of preventing implantation failure during assisted reproduction by administering to a subject GCSF mobilized peripheral blood stem cells, which can be histocompatible, as described above and in detail below. In this aspect of the invention, the blood stem cells are administered to a woman undergoing assisted reproduction. In particularly preferred embodiments, the administration is autologous, that is, the recipient subject is the same as the first female donor subject from whom the blood cells were collected. However, the administration can also be allogeneic, that is, the recipient subject is not the same as the first female donor subject. An amount of the blood stem cells effective to prevent implantation failure during assisted reproduction is administered to the subject according to methods known to practitioner of skill in the art.

In another embodiment, GCSF is administered to a subject undergoing assisted reproduction prior to or during ovarian stimulation to enhance the quality, viability and/or number of oocytes available for retrieval.

In a further aspect, the present invention provides methods of treating or preventing preeclampsia and preterm labor by administering to a subject in need thereof an effective amount of GCSF. The methods can be administered to any female subject at risk for preeclampsia or preterm labor. Subjects at risk can be identified according to the methods described herein or according to methods known to practitioners in the art. Typically, the subject is in the second or third trimester of pregnancy.

To treat or prevent preeclampsia and preterm labor, an effective amount of GCSF is administered to the subject. The GCSF can be administered by any mode of administration known to those of skill in the art. In certain embodiments, the GCSF is administered subcutaneously. The GCSF can be formulated in any preparation known to those of skill in the art for the mode of administration. The dose of GCSF can be determined by a practitioner of skill in the art as described in detail below. In certain embodiments, a dose of 10 µg/kg up through 500 mg is administered daily to the subject. The dose can be continued as long as necessary to treat or prevent preeclampsia pr preterm labor according to the judgment of the practitioner of skill in the art. In certain embodiments, the dose is administered through the end of pregnancy. In other embodiments, the dose is administered for four, three, two or one week. In particular embodiments, the dose is administered for five, four, three, two or one day.

As described above and in detail in the sections below, the methods, kits and compositions of the invention have utility for preventing spontaneous abortion, implantation failure and for treating or preventing preeclampsia or preterm labor.

DETAILED DESCRIPTION OF THE INVENTION

As used herein, the following terms shall have the following meanings:

The terms "treat", "treating" or "treatment" as used herein, refer to a method of alleviating or abrogating a disorder and/or its attendant symptoms. The terms "prevent", "preventing" or "prevention", as used herein, refer to a method of barring a subject from acquiring a disorder and/or its attendant symptoms. In certain embodiments, the terms "prevent", "preventing" or "prevention" refer to a method of reducing the risk of acquiring a disorder and/or its attendant symptoms.

The term "spontaneous abortion" refers to delivery or loss of the product of conception before the 20th week of pregnancy. The term spontaneous abortion includes but is not limited to miscarriage, threatened abortion, inevitable spontaneous abortion, incomplete spontaneous abortion, habitual or recurrent spontaneous abortion or missed abortion.

The term "miscarriage" is synonymous with spontaneous abortion.

The term "threatened spontaneous abortion" refers to any bleeding or cramping of the uterus in the first 20 weeks of pregnancy.

The term "inevitable spontaneous abortion" refers to bleeding or rupture of the membranes accompanied by pain and dilation of the cervix.

The term "incomplete spontaneous abortion" refers to expulsion of part of the products of conception or rupture of the membranes.

The term "habitual spontaneous abortion" or "recurrent spontaneous abortion" refers to three or more consecutive spontaneous abortions.

The term "missed abortion" refers to prolonged delay in expulsion of a dead fetus.

The term "assisted reproduction" refers to clinical and laboratory techniques used to enhance fertility in humans and animals, including, but not limited to, in vitro fertilization, GIFT, artificial insemination and the like.

The term "in vitro fertilization" refers to the procedure involving ovarian hyperstimulation, oocyte retrieval from the mother-to-be or a donor, fertilization outside the subject's body, embryo culture and embryo transfer. As used herein, embryo transfer refers to the procedure involving transfer to a subject's uterus, of the developing or cleaving embryos or pre-embryos, also termed preimplantation embryos.

The term "implantation failure" refers to the failure of an embryo produced by assisted reproduction to implant in the uterus of a recipient subject.

The term "preeclampsia" refers the development of hypertension with albuminuria or edema between the 20th week of pregnancy and the end of the first week postpartum. Any pregnant subject who develops a blood pressure of 140/90 mm Hg, edema of the face or hands or albuminuria of $\geq 1+$ or whose blood pressure rises by 30 mm Hg systolic or 15 mm Hg diastolic (even if less than 140/90 mm Hg) is considered preeclampsic.

The term "colony stimulating factor" or "CSF" relates to a growth factor that promotes and contributes to the maturity of cells, such as, hematopoietic and blood cells. Examples of CSF molecules include, but are not limited to, erythropoietin, GCSF, GMCSF, macrophage CSF, interleukin (IL)-3, IL-6 and stem cell factor.

The term "granulocyte-colony stimulating factor" or "G-CSF" refers to compounds or factors that stimulate proliferation, differentiation, commitment and end cell functional activation of granulocytes in an animal, including a human subject. G-CSF includes derivatives, mimetics, variants and chemically modified compounds or hybrids thereof as described in U.S. Pat. Nos. 5,399,345; 5,416,195; 5,981,551; 6,166,183 and 6,261,550, the contents of which are incorporated by reference in entireties. G-CSF is commercially available under the names filgrastim, (Neupogen®, Amgen and Granocyte®, Merck), pegfilgrastim (Neulasta®, Amgen) and lenograstim (Neutrogrin®, Chugai).

The term "granulocyte" refers to a blood cell containing granules, especially a leukocyte (white blood cell or corpuscle) containing neutrophil, basophil or eosinophil granules in its cytoplasm.

The term "granulocyte/macrophage colony stimulating factor" or "GMCSF" refers to compounds or factors that stimulate proliferation, differentiation, commitment and end cell functional activation of monocytes and granulocytes in an animal, including a human subject. GM-CSF includes derivatives, mimetics, variants and chemically modified compounds or hybrids thereof as described in, for example, U.S. Pat. Nos. 5,895,646; 5,891,429 and 5,908,763; the contents of which are incorporated by reference in entireties. GM-CSF is commercially available under the trade names Leukine®, Berlex and Leucomax®, Wyeth.

The term "macrophage" relates to a mononuclear, phagocytic cell that can exit the circulation and enter tissue spaces.

The term "therapeutically effective amount" refers to that amount of an active agent being administered sufficient to prevent development of or alleviate to some extent one or more of the symptoms of the condition or disorder being treated.

The term "preterm labor" also known as premature labor, refers to the beginning of regular contractions that cause the cervix to begin dilation and effacement before the 37th week of pregnancy.

The term "prophylactically effective amount" refers to that amount of an active agent being administered sufficient to prevent the disorder or prevent one or more symptoms of the disorder being treated. In certain embodiments, the term "prophylactically effective amount" refers to that amount of an active agent being administered sufficient to reduce the risk of the disorder or one or more symptoms of the disorder.

The term "subject" refers to animals such as mammals, including, but not limited to, primates (such as humans), cows, sheep, goats, horses, dogs, cats, rabbits, rats, mice and the like. In preferred embodiments, the subject is a human female.

The term "label" refers to a display of written, printed or graphic matter on the immediate container of an article, for example the written material displayed on a vial containing a pharmaceutically active agent.

The term "labeling" refers to all labels and other written, printed or graphic matter on any article or any of its containers or wrappers or accompanying such article, for example, a package insert or instructional videotapes or computer data storage devices, such as CDs and DVDs, accompanying or associated with a container of a pharmaceutically active agent.

The present invention is directed to methods of preventing spontaneous abortion and implantation failure and methods of treating or preventing preeclampsia described in detail below.

In one embodiment, the present invention provides methods of preventing spontaneous abortion by administering to a subject in need thereof a prophylactically effective amount of a GCSF.

While not intending to be bound by any particular theory of operation, it is believed that spontaneous abortion and recurrent spontaneous abortion are caused or associated with inappropriate immune responses in a pregnant subject. In particular, it is believed that subjects at risk for spontaneous abortion and recurrent spontaneous abortion present inappropriate immune cytokines associated with a T-helper 1 (Th1) immune response known to those of skill in the art. (See, Kwak-Kim et al., 2003, *Hum. Reprod.* 18(4): 676-773.) In contrast, subjects that have healthy pregnancies typically present immune cytokines associated with a T-helper 2 (Th2) immune response. It is believed that administration of GCSF can reduce the inappropriate Th1 response and/or increase a T-helper 2 (Th2) immune response in a subject. This invention is thus based, in part, on the discovery that administration of GCSF can shift a subject's immune response towards a healthy Th2 response during pregnancy and thereby reduce or eliminate the risk of spontaneous abortion.

The subject can be any mammalian subject at risk for a spontaneous abortion. In particularly preferred embodiments, the subject is a human female. In certain embodiments, the subject has previously had one or more spontaneous abortions. In further embodiments, the subject has previously had two or more spontaneous abortions. In other embodiments, the subject has had recurrent spontaneous abortions, i.e., three or more spontaneous abortions.

In further embodiments, the subject can be any subject in a population at risk for spontaneous abortion. For instance, the subject can be a human female in an age group at risk for spontaneous abortion. In particular embodiments, the subject can be a human female greater than 35 years of age, greater than 40 years of age or greater than 45 years of age. In other particular embodiments, the subject can be a human female less than 20 years of age or less than 15 years of age. However, essentially a woman of any age that presents with a reproductive infirmity, such as spontaneous abortion, preeclampsia and preterm labor, is a candidate for obtaining the materials and methods of the instant invention.

In further embodiments, the subject can also be in any other population at risk for spontaneous abortion as determined by a practitioner of skill in the art. In certain embodiments, the subject is threatening abortion. In other embodiments, the subject is obese, morbidly obese, has overall poor health or comorbid conditions that indicate a risk of spontaneous abortion to the skilled practitioner. In certain embodiments, these conditions can be incompetent cervix, uterine anomalies, hypothyroidism, diabetes mellitus, chronic nephritis, acute infection, use of illicit drugs (such as cocaine or crack), immunologic problems, severe emotional shock and viral infection (especially, cytomegalovirus, herpes virus and rubella) (see Merck Manual 17th edition, 1999, Merck Research Laboratories, Whitehouse Station, N.J., p. 2053). In certain embodiments, the subject has had an implantation failure during a previous assisted reproduction procedure. Other subjects at risk include those with unusually high Th1 immune responses or unusually low Th2 immune responses. In further embodiments, the subject can also be in any other population at risk for spontaneous abortion as determined by a practitioner of skill in the art.

In certain embodiments, the GCSF is administered to the subject prior to pregnancy. For instance, the GCSF is administered to a subject that is planning or attempting to become pregnant. In other embodiments, the GCSF is administered to a pregnant subject. The GCSF can be administered at any time during the first or second trimester of pregnancy. In preferred embodiments, the GCSF is administered during the first 20 weeks of pregnancy.

The GCSF can be any GCSF known to those of skill in the art to be effective in modulating the immune system of the subject. Thus, a range of modifications can be made to the wild-type GCSF molecules so long as the known immune system modulating activity of the GCSF is maintained. There are a number of assays that can be used to ensure that anyone modified GCSF retains the desired immune system modulating activity. The GCSF can be formulated according to any formulation for administration known to those of skill in the art. Plural types of GCSF molecules can be administered in the practice of the instant invention. The plural GCSF molecules can be administered consecutively or sequentially. In preferred embodiments, the GCSF formulation is the commercially available filgrastim (Neupogen® Amgen), peg-filgrastim (Neulasta®, Amgen) or lenograstim (Neutrogrin®, Chugai). Other effective GCSF molecules and formulations are described in detail in the sections below.

The GCSF formulation is administered in a prophylactically effective amount, i.e., an amount effective to reduce or eliminate the risk of spontaneous abortion in the subject. The amount can be determined by the skilled practitioner guided by the description herein and the knowledge in the art. In preferred embodiments, the amount can be any amount of GCSF that reduces the Th1 response of the subject. In further embodiments, the amount can be any amount sufficient to increase or initiate a Th2 response in the subject. Assays to determine Th1 and Th2 responses in the subject are well known to those of skill in the art (See Schust and Hill, 1996, *J. Soc. Gynecol. Investig.* 3:259-61, Xing et al., 2001, *Chin. Med. J.* 114:921-4, Raghupathy et al., 1999, *Cell Immunol.* 196:122-30, Mauri et al., 1996, *J. Immunol.* 26:1511-8, Doncorli et al., 1997, *Eur. J. Imm.* 27:1451-8, Raziuddin, 1998, *J. Rheumatol.* 25:329-33, Moverare et al., 2000, *Allergy* 55:171-5). In particular embodiments, a dose of 1 to 100 mcg/kg, 1 to 20 mcg/kg or about 10 mcg/kg is administered to the subject. In another embodiment, at least 25 mg, at least 50 mg, at least 75 mg, at least 100 mg, at least 125 mg, at least 150 mg, at least 175 mg, at least 200 mg, at least 300 mg or more is administered daily.

The dose can be administered to the subject daily until the risk of spontaneous abortion is reduced or eliminated and as long as no symptoms of toxicity are presented. In certain embodiments, the dose is administered daily through the second trimester of pregnancy. In further embodiments, the dose is administered daily through the 20th week of pregnancy. In particular embodiments, the dose is administered daily for four, three, two or one week during the first or second trimester of pregnancy. In particular embodiments, the dose is administered for five consecutive days during the first or second trimester of pregnancy. For example, the five consecutive days can be in the first or second week of pregnancy.

The GCSF can be administered according to any method of administration known to those of skill in the art. Preferred methods of administration include subcutaneous administration. Other effective modes of administration are described in detail in the sections below.

In another aspect, the present invention provides methods of preventing spontaneous abortion by administering to a subject in need thereof an effective amount of colony stimulating factor-mobilized peripheral blood stem cells.

While not intending to be bound by any particular theory of operation, as discussed above, it is believed that spontaneous abortion is caused or associated with an inappropriate Th1 immune response. It is believed that administration of peripheral blood stem cells can prevent spontaneous abortion by reducing the inappropriate Th1 immune response and/or increasing a Th2 immune response in a subject at risk for spontaneous abortion. It has been observed that GCSF can mobilize peripheral blood stem cells, and that these stem cells, when administered to a subject, can shift the subject's immune response toward a Th2 response. Thus, the present invention provides methods based, in part, on the discovery that GCSF mobilized stem cells can prevent spontaneous abortion.

The subject can be any mammalian subject at risk for a spontaneous abortion as described in the section above. In particularly preferred embodiments, the subject is a human female. In certain embodiments, the subject has previously had one or more, two or more, or three or more spontaneous abortions. In certain embodiments, the subject is threatening abortion or has had more than one threatened abortion. In further embodiments, the subject can be a human female greater than 35 years of age, greater than 40 years of age or greater than 45 years of age. In other particular embodiments, the subject can be a human female less than 20 years of age or less than 15 years of age. However, any woman of any age with imperfect reproductive fitness arising from, for example, spontaneous abortion, preeclampsia or preterm labor can obtain the benefits of the instant invention. In other embodiments, the subject is obese, morbidly obese, has overall poor health or comorbid conditions that indicate a risk of spontaneous abortion to the skilled practitioner. In certain embodiments, these conditions can be incompetent cervix, uterine anomalies, hypothyroidism, diabetes mellitus, chronic nephritis, acute infection, use of illicit drugs (such as cocaine or crack), immunologic problems, severe emotional shock and viral infection (especially cytomegalovirus, herpes virus and rubella) (see Merck Manual 17th edition, Merck Research Laboratories, p. 2053). Other subjects at risk include those with unusually high Th1 immune responses or unusually low Th2 responses. In further embodiments, the subject can also be in any other population at risk for spontaneous abortion as determined by a practitioner of skill in the art.

In the methods of this aspect of the invention, GCSF is administered to a first subject to mobilize peripheral blood stem cells that are to be collected for administration to a subject at risk for spontaneous abortion. In preferred embodiments, the peripheral blood stem cells, which can be histocompatible, comprise $CD34^+$ peripheral blood stem cells. Preferably, the first subject is a female that is not pregnant. In preferred embodiments, the methods are autologous. In these embodiments, peripheral blood stem cells are collected from the first subject and then administered to the same first subject. For instance, the cells can be collected while the subject is not pregnant, stored and later administered to the same subject before or after a positive pregnancy test. In other embodiments, the methods are allogeneic. The peripheral blood stem cells are collected from a first subject and administered to a second subject.

The GCSF can be any GCSF known to of skill in the art to be effective in mobilizing peripheral blood stem cells. The G-CSF can be formulated according to any formulation for administration known to those of skill in the art. In preferred embodiments, the G-CSF formulation is the commercially available (Neupogen® Amgen), pegfilgrastim (Neulasta® Amgen)) or lenograstim (Neutrogrin®, Chugai). Other effective G-CSF molecules and formulations are described in detail in the sections below.

The G-CSF formulation is administered in an amount effective to mobilize peripheral blood stem cells for collecting from the subject. The amount can be determined by the skilled practitioner guided by the description herein and the knowledge in the art. In preferred embodiments, the amount can be any amount of G-CSF that mobilizes peripheral blood stem cells. In particular embodiments, a dose of 1 to 100 mcg (micrograms)/kg, 1 to 20 mcg/kg or about 10 mcg/kg is administered to the subject.

In other embodiments, at least 25 mg; at least 50 mg; at least 75 mg; at least 100 mg; at least 125 mg; at least 150 mg; at least 175 mg; at least 200 mg; at least 300 mg or more GCSF is administered daily.

The dose can be administered to the subject daily for any time period necessary to mobilize peripheral blood stem cells as known to those of skill in the art. In certain embodiments, the dose is administered daily for four, three, two or one week. In particular embodiments, the dose is administered for five consecutive days. In other embodiments, the dose is administered daily for five, four, three, two or one day.

The G-CSF can be administered according to any method of administration known to those of skill in the art. Preferred methods of administration include subcutaneous administration. Other effective modes of administration are described in detail in the sections below.

In certain embodiments, the G-CSF is administered as a monotherapy. In other embodiments, the G-CSF is administered with at least one other active compound. The G-CSF and at least one other active compound can be administered simultaneously or sequentially, continuously or intermittently. For example, the other active ingredient can be administered according to the doses and schedules known to those of skill in the art while the G-CSF is administered according to the methods described herein. The at least one other active compound can be another CSF. The other active compound can be a drug currently used to treat the conditions of interest. The other active compound can be a drug that is an immunosuppressant. In preferred embodiments, the at least one other active ingredient is a chemotherapeutic or nonmyeloablative immunosuppressive agent. For example, the other active ingredient can be cyclophosphamide or a purine nucleoside analog such as cladribine and fludararbine. Preferred chemotherapeutic or nonmyeloablative immunosuppressive agents are described in detail in the sections below. The other active agent could also be another known immunosuppressive/anti-inflammatory agent such as vitamin D (or one of its analogs) or aspirin. In addition, the at least one other active agent could be one that is currently widely used for the treatment of Th1 cytokine excess in pregnancy, such as heparin, intravenous immunoglobulin (IVIG) or progesterone.

After an effective dose of G-CSF has been administered to the first subject, granulocytes are collected the first subject according to any method known to those of skill in the art. For example, whole blood can be collected from the first subject by any method known to those of skill in the art. Granulocytes, including peripheral blood stem cells, can be isolated from the whole blood by any method known to those of skill in the art such as cytophoresis or including, leukophoresis (also known as cytapharesis and leukapharesis). (See, *Guidelines for Therapeutic Hemapheresis*, revised May 1993, American Association of Blood Banks, Bethesda, Md.). Preferably, the granulocytes in these methods of the invention comprise peripheral blood stem cells, in particular, $CD34^+$ peripheral blood stem cells. Assays for $CD34^+$ cells are within the skill of those in the art. (see e.g., Link and Arseniev 1997, *Leuk. Lymphoma* 26:451-65, Vogel et al., 2000, *Stem Cells* 18:87-92, Dreger et al., 1994, *Br. J. Haematol.* 87:609-613; and Berenson et al., 1996, *Cancer Invest.* 14:589-96)

In certain embodiments, these granulocytes can be stored for later administration to the first subject or to another subject. Although cryopreservation is the primary method of storing granulocytes, other methods are being developed for the long term storage of blood cells and can be used in the methods of invention. (See, for example, U.S. Pat. No. 6,150, 085, Papadimitriou et al., 2000, *J Clin. Apheresis* 15:236-24: 236-241; Arpaci et al., 2000, *Jpn. J Clin. Oncol.* 30: 154-88). Formulations and methods of storage such as cryogenic preservation are well known to those of skill in the art. The collected granulocytes can optionally be formulated for administration to a subject prior to storage or after storage.

In these methods of the invention, the collected granulocytes are administered to a subject to prevent spontaneous abortion. In certain embodiments, the cells are administered to the subject prior to pregnancy. For instance, the cells can be administered to a subject that is planning or attempting to become pregnant. In other embodiments, the cells are administered to a pregnant subject. The cells can be administered at any time during the first or second trimester of pregnancy. In preferred embodiments, the cells are administered during the first 20 weeks of pregnancy.

The cells are administered in a prophylactically effective amount, an amount effective to reduce or eliminate the risk of spontaneous abortion in the subject. The amount can be determined by the skilled practitioner guided by the description herein and the knowledge in the art. In preferred embodiments, the amount can be any amount of cells that reduce the Th1 response of the subject. In further embodiments, the amount can be any amount sufficient to increase or initiate a Th2 response in the subject. Assays to determine Th1 and Th2 responses in the subject are well known to those of skill in the art (See e.g., Schust and Hill, 1996, *J. Soc. Gynecol. Investig.* 3:259-61, Xing et al., 2001, *Chin. Med. J.* 114:921-4, Raghupathy et al., 1999, *Cell Immunol.* 196:122-30, Mauri et al, 1996, *Eur. J. Immunol.* 26:1511-8, Doncarli et al, 1997, *Eur. J. Immunol.* 27:1451-8, Raziuddin, 1998, *J. Rheumatol.* 25:329-33, Moverare et al., 2000, *Allergy* 55:171-5). In particular embodiments, about 250-750 ml of collected leukapheresis material or about 5 to 15×106 CD34+ cells is administered to the subject.

The cells can be administered to the patient daily until the risk of spontaneous abortion is reduced or eliminated and as long as no symptoms of toxicity are presented. In certain embodiments, the cells are administered daily through the second trimester of pregnancy. In further embodiments, the cells are administered daily through the 20th week of pregnancy. In particular embodiments, the cells are administered daily for four, three, two or one week during the first or second trimester of pregnancy.

The peripheral blood stem cells can be administered according to any method of administration known to those of skill in the art. Preferred methods of administration of blood stem cells include intravenous administration.

In another aspect, the present invention provides methods of preventing embryo implantation failure during assisted reproduction by administration to a subject in need thereof a prophylactically effective amount of granulocyte colony stimulating factor.

In vitro fertilization is an assisted procedure to overcome fertility problems caused by, for example, tubal disease, endometriosis, oligospermia, sperm antibodies and unexplained infertility. The procedure can include ovarian hyperstimulation with 'fertility drugs' such as ovarian stimulants like clomiphene citrate and gonadotropin-releasing hormones. Hyperstimulation of the ovaries can induce growth of the egg (oocyte) and its encasing cells, collectively also termed the ovarian follicles. After sufficient follicular growth, final follicular maturation is induced and oocytes are retrieved or harvested. The oocytes are fertilized in vitro with sperm and the embryos cultured. A small number of embryos, generally 2-4, are then transferred to the uterus. Despite the transfer of multiple embryos, the term pregnancy rate is only about 25%. (see Merck Manual 17$^{th}$ edition, 1999, Merck Research Laboratories, Whitehouse Station, N.J. p.1995).

While not intending to be bound by any particular theory of operation, it is believed that implantation failure during assisted reproduction is caused or associated with inappropriate immune responses in the embryo recipient. In particular, it is believed that subjects at risk for embryo implantation failure present with an overproduction of T-helper 1 (Th1) cytokines and underproduction of T-helper 2 (Th2) cytokines Positive correlations in human and animal models have been demonstrated, (see, Kwak-Kim et al., 2003, *Human Reproduction* 18:767-73, Krishnan et al., 1996, *J. Immunol.* 156: 653-62) but remain controversial (see, Chaouat et al., 2003, *J. Reproductive Immunol.* 59:205-17). The Th1 cytokine associated with overproduction can be interferon-γ(INF-γ). The Th2 cytokines associated with underproduction can be interleukins 10 and 4 (IL-10 and IL-4).

In the methods of prevention, the G-CSF is typically administered until implantation of the embryo to the uterine wall is achieved, until the risk of failed implantation is reduced or eliminated or according to the judgment of a practitioner of skill in the art.

In certain embodiments, the administration is continued until pregnancy is confirmed. In certain embodiments, the administration is started about the time of ovarian hyperstimulation and continued until about 3 days, about 5 days, about 7 days, about 10 days, about 12 days, about 14 days or about 30 days after embryo transfer to the subject's uterus. In certain embodiments, the administration is started about the time of ovarian hyperstimulation and continued until about the end of the first trimester. In another embodiment, the dose is administered for five consecutive days about the time of embryo transfer to the subject's uterus. In certain embodiments, the administration is continued until the subject presents a normal Th1 immune response for a pregnant subject or a normal Th2 immune response for a pregnant subject, or both, according to the judgment of a practitioner of skill in the art.

In certain embodiments, a prophylactically effective amount of GCSF is administered to a subject at risk of embryo implantation failure. In certain embodiments, a subject at risk is a subject that has failed one or more in vitro fertilization procedures. In further embodiments, the subject can also be in any other population at risk for failed embryo implantation as determined by a practitioner of skill in the art. In certain embodiments, the subject has previously failed assisted reproduction. In another embodiment, the subject has had one or more previous spontaneous abortions. Other subjects at risk include those with unusually high Th1 immune responses or unusually low Th2 immune responses. In further embodiments, the subject can also be in any other population at risk for failed embryo implantation as determined by a practitioner of skill in the art.

In certain embodiments, the G-CSF is administered to the subject prior to embryo transfer. For instance, the G-CSF is administered to a subject that is planning or attempting to become pregnant via assisted reproduction. Thus, the GCSF can be administered to the mother-to-be during the superovulation procedure or if ova are donated, prior to implantation of the embryos. In other embodiments, the G-CSF is administered to a subject after retrieving or harvesting oocytes. In another embodiment, the retrieved oocytes and the embryos are maintained and cultured in medium containing GCSF prior to being instilled in the mother-to-be. The G-CSF can be administered at any time during the assisted reproduction or in vitro fertilization process.

The G-CSF can be any G-CSF known to those of skill in the art to be effective in modulating the immune system of the subject. The G-CSF can be formulated according to any formulation for administration known to those of skill in the art. In preferred embodiments, the G-CSF formulation is the commercially available filgrastim (Neupogen®, Amgen), pegfilgrastim (Neulasta®, Amgen) or lenograstim (Neutrogrin®, Chugai). Other effective G-CSF molecules and formulations are described in detail in the sections below.

The G-CSF formulation is administered in a prophylactically effective amount, i.e., an amount effective to reduce or eliminate the risk of implantation failure in the subject. The amount can be determined by the skilled practitioner guided by the description herein and the knowledge in the art. In preferred embodiments, the amount can be any amount of G-CSF that reduces the Th1 response of the subject. In further embodiments, the amount can be any amount sufficient to increase or initiate a Th2 response in the subject. In particular embodiments, a dose of 1 to 100 mcg/kg, 1 to 20 mcg/kg or about 10 mcg/kg is administered daily to the subject. In other embodiments, at least 25 mg; at least 50 mg; at least 75 mg; at least 100 mg; at least 125 mg; at least 150 mg; at least 175 mg; at least 200 mg; at least 300 mg or more GCSF is administered daily.

The G-CSF can be administered according to any method of administration known to those of skill in the art. Preferred methods of administration include subcutaneous administration. Other effective modes of administration are described in detail in the sections below.

In another aspect, the present invention provides methods of preventing implantation failure during assisted reproduction by administering to a subject G-CSF mobilized peripheral blood stem cells. In this aspect, G-CSF is administered to a first female subject and peripheral blood stem cells, particularly CD34+ peripheral blood stem cells are collected from the first subject as described herein. In particularly preferred embodiments, the administration is autologous. However, the administration can also be allogeneic, i.e., the recipient subject is not the same as the first female donor subject. An amount of the blood stem cells, which can be histocompatible, effective to prevent implantation failure during assisted reproduction is administered to the subject according to methods described above. In another aspect, the present invention provides methods of preventing implantation failure during assisted reproduction by administering G-CSF mobilized peripheral blood stem cells to a subject prior to ovarian hyperstimulation. In another aspect, the present invention provides methods of administering about 250-750 ml of collected leukapharesis material or about 5 to $15 \times 10^6$ CD34 cells to the subject. In another aspect, the present invention provides for administration of peripheral blood stem cells from about the time of ovarian hyperstimulation and continued until about 3 days, about 5 days, about 7 days, about 10 days, about 12 days, about 14 days or about 30 days after embryo transfer to the subject's uterus.

In a further aspect, the present invention provides methods of treating or preventing preeclampsia or preterm labor by administering to a subject in need thereof an effective amount of granulocyte colony stimulating factor.

While not intending to be bound by any particular theory of operation, it is believed that preeclampsia and preterm labor is caused or associated with inappropriate immune responses in a pregnant subject. In particular, it is believed that subjects at risk for preeclampsia or preterm labor present inappropriate immune cytokines associated with a T-helper 1 (Th1) immune response known to those of skill in the art. In contrast, subjects that have healthy pregnancies typically present immune cytokines associated with a T-helper 2 immune response. It is believed that administration of G-CSF can reduce the inappropriate Th1 response and/or increase a Th2 immune response in a subject. This invention is thus based, in part, on the discovery that administration of G-CSF can shift a subject's immune response towards a healthy Th2 response during pregnancy and thereby treat or prevent preeclampsia or preterm labor.

In the methods of treatment, G-CSF is administered to a subject presenting one or more symptoms of preeclampsia or preterm labor. The subject can be any subject that presents any of the symptoms of preeclampsia during pregnancy such as hypertension, swelling or edema and excessive protein in the urine. For example, the subject can be any subject that develops hypertension with albuminuria or edema between the 20th week of pregnancy and the end of the $1^{st}$ week postpartum. Particular subjects include pregnant females who develop a blood pressure of 140/90 mm Hg, edema of the face or hands or albuminuria of ≧1+ or whose blood pressure rises by 30 mm Hg systolic or 15 mm Hg diastolic (even if less than 140/190 mm Hg) between the 20th week of pregnancy and the end of the 1st week postpartum. Particularly preferred subjects are human females.

In the methods of treatment, the G-CSF is typically administered until the symptoms of preeclampsia or preterm labor are alleviated or reduced as long as the therapeutic benefit outweighs the risk of adverse events according to the judgment of a practitioner of skill in the art. The dosing can continue as long as the subject displays no toxic effects of the administration according to the judgment of a practitioner of in the art. In certain embodiments, the treatment is continued until the subject presents a normal Th1 immune response for a pregnant subject or a normal Th2 response for a pregnant subject, or both, according to the judgment of a practitioner of skill in the art.

In the methods of prevention, G-CSF is administered to a subject at risk for developing preeclampsia or preterm labor. The subject can be any mammalian subject at risk for preeclampsia or preterm labor. Subjects at risk include subjects carrying multiple babies, subjects younger than age 20 and subjects older than age 40. Further subjects include those pregnant for the first time (primigravida), subjects with preexisting hypertension and subjects with preexisting vascular disease. Other subjects at risk include those with unusually high Th1 immune responses or unusually low Th2 immune responses. In particularly preferred embodiments, the subject is a human female.

In the methods of prevention, G-CSF is administered as long as the subject is at risk for preeclampsia and as long as the therapeutic benefit outweighs the risk of adverse events and also, so long as no toxicity is observed according to the judgment of a practitioner of skill in the art. In certain embodiments, G-CSF is administered for the duration of the pregnancy. In particular embodiments, administration is provided in the 2nd and 3rd trimester of pregnancy. In further embodiments, administration is continued after delivery for about one, about two, about three, about four, about five, about six, about seven or about eight weeks post partum. In certain embodiments, the treatment is continued until the subject presents a normal Th1 immune response for a pregnant subject or a normal Th2 immune response for a pregnant subject, or both, according to the judgment of a practitioner of skill in the art.

The G-CSF can be any G-CSF known to those of skill in the art to be effective in modulating the immune system of the subject as described in the sections above. The GCSF can be formulated according to any formulation for administration known to those of skill in the art. In preferred embodiments, the G-CSF is the commercially available filgrastim or pegfilgrastim. Other effective G-CSF molecules and formulations are described in detail in the sections below.

The G-CSF formulation is administered in a prophylactically or therapeutically effective amount, i.e., an amount effective to prevent or reduce or eliminate the preeclampsia or the symptoms of preeclampsia in the subject. The amount can be determined by the skilled practitioner guided by the description herein and the knowledge in the art. In preferred embodiments, the amount can be any amount of G-CSF that reduces the Th1 response of the subject. In further embodiments, the amount can be any amount sufficient to increase or initiate a Th2 response in the subject. Assays to determine Th1 and Th2 responses in the subject are well known to those of skill in the art (See e.g., Schust and Hill, 1996, *J Soc. Gynecol. Investig.* 3:259-61, Xing et al., 2001, *Chin. Med. J*114:921-4, Raghupathy et al., 1999, *Cell Immunol*. 196:122-

30, Mauri et al., 1996 *Eur. J Immunol.* 26:1511-8, Doncarli et al., 1997, *Eur. J Immunol.* 27:1451-8, Raziuddin, 1998, *J. Rheumatol.* 25:329-33, Moverare et al., 2000, *Allergy* 55:171-5). In particular embodiments, a daily dose of 1 to 100 mcg/kg, 1 to 20 mcg/kg or about 10 mcg/kg is administered to the subject. In other embodiments, at least 25 mg; at least 50 mg; at least 75 mg; at least 100 mg; at least 125 mg; at least 150 mg; at least 175 mg; at least 200 mg; at least 300 mg or more GCSF is administered daily.

The G-CSF can be administered according to any method of administration known to those of skill in the art. Preferred methods of administration include subcutaneous administration. Other effective modes of administration are described in detail in the sections below.

While generally a medical history will serve to ascertain candidate subjects in need of treatment as described herein, diagnostic assays can be used to ascertain subjects presenting with reproductive inefficiencies that are correlated with particular immunologic parameters. As noted herein, patients with repeated spontaneous abortion or miscarriage, preeclampsia, preterm labor and the like present with particular profiles of their immune system status. Thus, subjects with high Th1 cell number or cell activity and/or reduced Th2 cell number or cell activity, or an aberrant ratio of the two may be candidates for obtaining the instant treatment of interest.

Hence, a diagnostic assay of interest is one that determines whether Th1 cell number or cell activity is enhanced. Another assay of interest is one that determines whether Th2 cell number or activity is decreased. Yet another assay of interest is one that determines a higher ratio of Th1 cell number to Th2 cell number, or Th1 cell activity to Th2 cell activity.

A number of known assays, for example, immunoassays or bioassays, can be used to make such determinations. For example, γ interferon, tumor necrosis factor β and IL-2 are markers of Th1 cells. Thus, assays for one or more of such cell-specific markers can provide the basis to conclude a higher than normal Th1 status. As to Th2, IL-4, IL-5, IL-6, IL-10 and IL-13 are known markers of that cell type. Thus, assays for one or more of such cell-specific markers can provide the basis to conclude a higher than normal Th2 status.

As described in detail above, the present invention provides methods of administering an effective amount of granulocyte colony stimulating factor (G-CSF) to prevent abortion, implantation failure during assisted reproduction or to treat or prevent preeclampsia or preterm labor.

The G-CSF administered in the methods of the invention can be any G-CSF known to one of skill in the art without limitation. In certain embodiments, the G-CSF can be any G-CSF or any derivative, variant, mimetic, chemically modified version or hybrid thereof, as described in U.S. Pat. Nos. 5,399,345; 5,416,195; 5,981,551; 6,166,183 and 6,261,550, the contents of which are hereby incorporated by reference in their entireties. In further embodiments, the G-CSF can be administered in the form of a nucleotide sequence encoding G-CSF or expression vectors encoding G-CSF described in U.S. Pat. No. 5,422,248, the content of which is hereby incorporated by reference in its entirety.

In certain embodiments, the G-CSF is a commercially available G-CSF available as a pharmaceutical composition, suitable for administration to an animal, including a human. Such commercially available pharmaceutical compositions can be, for example, filgrastim (Neupogen®, Amgen), pegfilgrastim (Neulasta®, Amgen) or lenograstim (Neutrogrin®, Chugai).

Filgrastim and lenograstim are useful for promoting neutrophil proliferation and is generally administered to individuals in need to increased neutrophils, for example, patients undergoing chemotherapy. Filgrastim and lenograstim are indicated for myelosuppressive chemotherapy, bone marrow transplant, peripheral blood progenitor cell collection and severe chronic neutropenia. Off label uses include treatment of neutropenia in AIDS patients, aplastic anemia, hairy cell leukemia, myelodysplasia, drug-induced and congenital agranulocytosis and alloimmune neonatalneutropenia.

The usual treatment of myelosuppressive is 5 mcg/kg/day, once daily either by bolus subcutaneously or short (15-30 minute) intravenous infusion or by continuous subcutaneous or intravenous infusion. Administration is once daily starting no earlier than 24 hours after chemotherapy and continues for 14 days or until the individual's absolute neutrophil count is 10,000/mm$^3$. For patients undergoing bone marrow transplant, the usual dose is 10 mcg/kg/day administered as an intravenous infusion over 4-24 hours or as a continuous 24 hour subcutaneous infusion. The first dose is generally administered at least 24 hours after chemotherapy and at least 24 hours after bone marrow infusion. During recovery, the dose is adjusted by 5 mcg/kg/day titrating to the patient's absolute neutrophil count. Filgrastim dosing for peripheral blood progenitor cells generally begins at 10 μg/kg/day subcutaneously either as a bolus or continuous infusion. It is recommended that filgrastim be given for at least four days before leukapheresis and continued until the last leukapheresis procedure. Doses of filgrastim for congenital neutropenia are 6 mcg/kg subcutaneously twice daily while idiopathic or cyclic neutropenia is generally treated with a dose of 5 mcg/kg subcutaneously once daily.

Pegfilgrastim is a monomethoxypolyethylene glycol conjugate of filgrastim. The pharmaceutical composition is commercially available as preservative free solutions of 10 mg/ml pegfilgratim in prefilled single-dose syringes. Pegfilgrastim is indicated to decrease infections in patients with febrile neutropenia undergoing myelosuppressive chemotherapy. Recommended dosing is a single 6 mg subcutaneous injection administered once per chemotherapy cycle.

In certain embodiments described above, the present invention provides methods administering to a subject in need thereof an effective amount of G-CSF as monotherapy. In other embodiments, the present invention provides methods of administering to a subject an effective amount of G-CSF in combination with at least one other active agent. Other active agents include myeloablative immunosuppressive therapy.

In one aspect, the non-myeloablative immunosuppressive therapy can be any non-myeloablative immunosuppressive therapy available to one of skill in the art. In one aspect, the immunosuppressive therapy can be one or more antineoplastic or chemotherapeutic agents including, but not limited to, alkylating agents, antimetabolites, antimitotic agents, epipodophyllotoxins, antibiotics, hormones, enzymes, platinum coordination complexes, anthracenediones, substituted ureas, methylhydrazine derivatives and topoisomerases, as described, for example, in U.S. Pat. No. 6,162,417, incorporated herein by reference in its entirety. Examples of such antineoplastic or chemotherapeutic agents include, but is not limited to, chlorambucil (Leukeran®, GlaxoWellcome), cyclophosphamide (Cytoxan®, Mead Johnson), mechlorethamine (Mustargen®, Merck), melphalan (Alkeran®, Glaxo Wellcome), busulfan (Myerlan®, Glaxo Wellcome), methotrexate (various), cytarabine (various), fluorouracil (5-fluorouracil) (various, including Adrucil®, Pharmacia Upjohn), cladribine (2-chlorodeoxyadenosine, Leustain®, OrthoBiotech), fludarabine (Fludara®, Berlex) hydroxyurea (Hydrea®, Bristol-Myers Squibb), asparaginase (Elspar®, Berlex), mitoxantrone Novantrone®, Immunex) and procarbazine (Matulane®, Roche). In one aspect, the immunosuppressive therapy can be an immunosuppressive agent not generally used as a antineoplastic or chemotherapeutic agent. Such immunosuppressive agents caube alefacept (Amevive®, Biogen), azathioprine (Imura®, GlaxoWellcome), basiliximab (Simulect®, Novartis), cyclosporin (Sandimmune® and Neoral®, Sandoz) daclizumab (Zenapax®, Roche), glatiramer (Copaxone®, TEV A), muromonab-CD3 (Orthoclone OKT3®, Ortho Biotech), mycophenolate (CellCept®, Roche), tacrolimus (Prograf®, Fujisawa) and sirolimus (Rapamune®, Wyeth Labs). The appropriate immunosuppressive or chemotherapeutic agent can be selected by one of skill in the art based on the individual, for example, comorbid medical conditions, overall subject health and age.

Other at least one other active agents to be used with a GCSF include an anti-inflammatory agent. The anti-inflammatory agent can be one that reduces leukocyte populations. Other anti-inflammatory agents can be used as well. For example, vitamin D3 (1,25-dihydroxycholecalciferol) and analogs thereof can be used.

Other at least one other active agents to be used with a GCSF are those currently used to treat recurring spontaneous abortion or miscarriage, preeclampsia, IVIG implantation failure or preterm labor, such as intravenous Ig and heparin.

The invention provides methods of administering compositions of G-CSF useful for preventing spontaneous abortion or implantation failure or treating or preventing preeclampsia or preterm labor. In the compositions administered, the G-CSF can be formulated in any manner known to those of skill in the art for formulating and administering effective amounts of G-CSF. Preferred formulations include commercially available formulations.

Filgrastim or G-CSF is available as a preservative pharmaceutical composition comprising 300 mcg/ml. The composition can be administered subcutaneously without further admixture. Intravenous preparations require dilution with proper diluent, such as 5% dextrose, diluted to a final concentration of filgrastim of 5 to 15 mcg/ml. Saline is not recommended as a diluent due to product precipitation. Mixture with albumin is recommended to prevent adsorption to plastic materials during preparation and infusion. The final concentration of human albumin should be 2 mg/ml. It is highly recommended that filgrastim be refrigerated at 2° to 8° C.

The presently available pharmaceutical composition contains a small amount of acetate, Tween 80 and sodium. These excipients are used to achieve and maintain characteristics that are physiologically acceptable to the body and pharmaceutically practical and elegant. Such characteristics include, tonicity, osmoticity, osmolality, osmolarity, viscosity and shelf life. Aqueous pharmaceutical compositions of G-CSF with increased half life have been described, for example, in U.S. Pat. No. 5,919,757, incorporated herein by reference in its entirety.

The pharmaceutical compositions can comprise the G-CSF in a salt form. For example, because proteins can comprise acidic and/or basic termini side chains, the proteins can be included in the pharmaceutical compositions in either the form of free acids or bases, or in the form of pharmaceutically acceptable salts. Pharmaceutically acceptable salts can include, suitable acids which are capable of forming salts with the proteins of the present invention including, for example, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, cinnamic acid, anthranilic acid, citric acid, naphthalene sulfonic acid, sulfanilic acid and the like. Suitable bases capable of forming salts with the subject proteins can include, for example, inorganic bases such as sodium hydroxide, ammonium hydroxide, potassium hydroxide and the like; and organic bases such as mono-, di- and tri-alkyl amines (for example, triethyl amine, diisopropyl amine, methyl amine, dimethyl amine and the like) and optionally substituted ethanolamines (for example, ethanolamine, diethanolamine and the like).

Although commercially available G-CSF is currently administered subcutaneously or intravenously, any method of administration that provides a therapeutically effective amount of G-CSF can be used in the methods of the invention. In one aspect, G-CSF can be in a variety of forms suitable for any route of administration, including, but not limited to, parenteral, enteral, topical or inhalation.

Parenteral administration refers to any route of administration that is not through the alimentary canal, including, but not limited to, injectable administration, i.e., intravenous, intramuscular and the like as described below. Enteral administration refers to any route of administration which is oral, including, but not limited to, tablets, capsules, oral solutions, suspensions, sprays and the like, as described below. For purposes of this invention, enteral administration also refers to rectal and vaginal routes of administration. Topical administration refers to any route of administration through the skin, including, but not limited to, creams, ointments, gels and transdermal patches, as described below (see also, Pharmaceutical Sciences, 18th Edition (Gennaro et al., eds., Mack Printing Company, Easton, Pa., 1990).

Parenteral pharmaceutical compositions of the present invention can be administered by injection, for example, into a vein (intravenously), an artery (intraarterially), a muscle (intramuscularly) or under the skin (intradermal or subcutaneous) or in a depot composition.

Injectable pharmaceutical compositions can be sterile suspensions, solutions or emulsions of the G-CSF in aqueous or oily vehicles. The compositions can also comprise formulating agents or excipients, such as suspending, stabilizing and/or dispersing agents. The formulations for injection can be presented in unit dosage form, in ampules or in multidose containers, and can comprise added preservatives. In certain embodiments, the pharmaceutical compositions contain buffers such as citrate, acetate, phosphate, tris(hydroxymethyl) amino methane or THAM (tromethamine).

Depot or sustained release pharmaceutical compositions can be used in the methods of the invention. For example, continuous release of G-CSF can be achieved by the conjugation of the G-CSF with a water soluble polymer as described in U.S. Pat. No. 5,320,840.

Injectable compositions can be pharmaceutically appropriate compositions for any route of injectable administration, including, but not limited to, intravenous, intrarterial, intracoronary, pericardial, perivascular, intramuscular, subdermal, subcutaneous and intraarticular.

Alternatively, the injectable pharmaceutical composition can be provided in powder form for reconstitution with a suitable vehicle, including but not limited to sterile pyrogen free water, buffer, dextrose solution, etc., before use. To this end, the G-CSF can be lyophilized as appropriate. The pharmaceutical compositions can be supplied in unit dosage forms and reconstituted prior to use in vivo.

For prolonged delivery, the pharmaceutical composition can be provided as a depot preparation, for administration by implantation; e.g., subcutaneous, intradermal, or intramuscular injection. Thus, for example, the pharmaceutical composition can be formulated with suitable polymeric or hydrophobic materials as an emulsion in an acceptable oil) or ion exchange resins, or as sparingly soluble derivatives; as a sparingly soluble salt form of the G-CSF, or derivative, mimetic or variant thereof. The GCSF can be present in an inert matrix or device for implantation to achieve prolonged release.

Alternatively, transdermal delivery systems manufactured as an adhesive disc or patch that slowly releases the active ingredient for percutaneous absorption can be used. To this end, permeation enhancers can be to facilitate penetration of the G-CSF. A particular benefit may be achieved by incorporating the G-CSF into a transdermal patch.

For oral administration, the pharmaceutical formulations can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art (see, Remington's Pharmaceutical Sciences, 18th edition (Gennaro et al., eds.) Mack Printing Company, Pa., 1990).

Liquid pharmaceutical compositions for oral administration can take the form of, for example, solutions, syrups or suspensions, or they can be a dry product for constitution with water or other suitable vehicle before use. Such liquid pharmaceutical compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid.).

The pharmaceutical compositions can also comprise buffer salts, flavoring, coloring and sweetening agents as appropriate. Pharmaceutical compositions for oral administration can be suitably prepared to provide controlled release of the G-CSF.

Enteral pharmaceutical compositions can be suitable for buccal administration, for example, in the form of tablets, troches or lozenges. For rectal and vaginal routes of administration, the G-CSF can be prepared as solutions (e.g. for retention enemas) suppositories or ointments. Enteral pharmaceutical compositions can be suitable for admixture in feeding mixtures, such as, for mixture with total parenteral nutrition (TPN) mixtures or for delivery by a feeding tube (see, Dudrick et at, 1998, *Surg. Technol. Int.* VII: 174-184; Mohandas et at, 2003, *Natl. Med. J India* 16(1):29-33; Bueno et al., 2003, *Gastrointest. Endosc.* 57(4):536-40; Shike et al., 1996, *Gastrointest. Endosc.* 44(5):536-40).

For administration by inhalation, the G-CSF can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of e.g., gelatin for use in an inhaler or insufflator can be formulated comprising a powder mix of the compound and a suitable powder base such as lactose or starch. Inhaled pharmaceutical compositions can be those, for example, described in U.S. Pat. Nos. 5,284,656 and 6,565,841, incorporated herein by reference in their entirety.

The compositions can, if desired, be presented in a pack or dispenser device that can comprise one or more unit dosage forms comprising the G-CSF. The pack can for example comprise metal or plastic foil, such as a blister pack. The pack or dispenser device can be accompanied by instructions for administration.

The pharmaceutical compositions can be for a single, one time use or can contain antimicrobial excipients, rendering the composition suitable for multiple, extended use with greater shelf stability, for example, a multi-use bottle. In another embodiment, the pharmaceutical composition of interest can be in unit dose or unit-of-use packages. As known in the art, a unit dose is targeted for a single use. The unit dose form can be in a vial, which can contain a solution or a desiccated form for reconstitution, a pre-filled syringe, a transdermal patch and the like.

As is known to those of skill in the art, a unit-of-use package is a convenient prescription size, patient ready unit labeled for distribution by health care providers. The package contains as much active ingredient necessary for a typical treatment regimen.

The pharmaceutical composition can be labeled and have accompanying labeling to identify the composition contained therein and other information useful to health care providers and end users. The information can include instructions for use, dose, dosing interval, duration, indication, side effects and other contraindications, warnings, precautions, storage recommendations and the like.

Various embodiments of the pharmaceutical compositions have been described. The descriptions and examples are intended to be illustrative of the invention and not limiting. Indeed, it will be apparent to those of skill in the art that modifications to the pharmaceutical compositions can be made to the various embodiments of the invention described without departing the spirit of the invention.

The invention provides methods of administering compositions of G-CSF useful for preventing spontaneous abortion, implantation failure during assisted reproduction or treating or preventing preeclampsia. The G-CSF and G-CSF compositions can be administered by any route or on any schedule which provides a therapeutically or prophylactically effective amount of G-CSF.

In one aspect the G-CSF or G-CSF compositions can be administered parenterally, for example, subcutaneously or intravenously. The parenteral administration can be in a single bolus or as a continuous infusion. In one aspect the parenteral administration can be a single intravenous infusion given over 15-30 minutes. In another aspect the parenteral administration can be a continuous infusion of G-CSF diluted in 5% dextrose.

The methods provide for administration of G-CSF for a therapeutically or prophylactically effective time. In certain embodiments, the G-CSF is administered prior to the onset or observation of the disorder or symptoms accompanying the disorder. In further embodiments, the G-CSF is administered during the disorder or during the time period that symptoms accompanying the disorder are observed. In other embodiments, the G-CSF is administered for a time after the disorder had cleared. For example, the G-CSF can be administered about one day, about two days, about three days, about four days, about one week, about two weeks and up to about eight weeks, following resolution of the preeclampsia, signs of preterm labor, threatened abortion or after confirmation of pregnancy during assisted reproduction.

In another aspect, the present invention provides kits for carrying out the methods of the invention. For example, the present invention provides kits for preventing spontaneous abortion or implantation failure during assisted reproduction. The kits comprise one or more effective doses of G-CSF along with a label or labeling with instructions on using the G-CSF to prevent spontaneous abortion or implantation failure during assisted reproduction according to the methods of the invention. In certain embodiments, the kits can comprise components useful for carrying out the methods such as devices for delivering the G-CSF. In certain embodiments, the kit can comprise components useful for the safe disposal of devices for delivering the G-CSF, e.g., a sharp container for used syringes.

In other embodiments, the present invention provides kits for preventing spontaneous abortion or implantation failure during assisted reproduction by administering mobilized $CD34^+$ peripheral blood stem cells. These kits comprise one or more effective doses of G-CSF along with a label or labeling with instructions on using the G-CSF to mobilize $CD34^+$ peripheral blood stem cells according to the methods of the invention. The kits can also comprise a label or labeling with instructions for collecting and/or storing peripheral blood stem cells. In certain embodiments, the kits comprise a myeloablative immunosuppressive agent described above. These kits can also comprise components useful for carrying out the methods such as devices for delivering the G-CSF and components for the safe disposal of these devices. The kits can also comprise devices for collecting blood stem cells and devices and formulations for storing blood stem cells.

In further embodiments, the present invention provides kits for preventing spontaneous abortion or implantation failure during assisted reproduction by administering G-CSF-mobilized peripheral blood stem cells to a subject. The kits comprise a device for administering peripheral blood stem cells along with instructions for administering G-CSF-mobilized peripheral blood stem cells to a subject to prevent spontaneous abortion or implantation failure during assisted reproduction. In certain embodiments, the present invention provides kits comprising the components of the kits for mobilizing $CD34^+$ peripheral blood stem cells and the components of for administering G-CSF-mobilized peripheral blood stem cells to a subject.

In further embodiments, the present invention provides kits for treating or preventing preeclampsia or preterm labor. The kits comprise one or more effective doses of G-CSF along with a label or labeling with instructions on using the G-CSF to treat or prevent preeclampsia or preterm labor according to the methods of the invention. In certain embodiments, the kits can comprise components useful for carrying out the methods such as devices for delivering the G-CSF and components for the safe disposal of these devices.

In further embodiments, the instant invention provides kits for treating or preventing preterm labor. The kits comprise one or more effective doses of GCSF along with a label or labeling with instructions on using the GCSF to treat or prevent preterm labor according to the methods of the invention. In certain embodiments, the kits can comprise components useful for carrying out the methods such as devices for delivering the GCSF and components for the safe disposal of the devices.

The invention now will be exemplified in the following non-limiting examples.

Example 1

G-CSF Prevents Embryotoxic Effects of Cells from Women with Recurrent Spontaneous Abortion in Vitro G-CSF is effective in preventing the death of mouse embryos in an in vitro clinical assay for spontaneous abortion. Mouse bioassays have widely been used to detect embryotoxic effects of sera from subjects having reproductive difficulty. (See, Cameo, et al., 1999, *Human Reprod.* 14(4):959-63, Oksenberg and Brautbar 1986, *Am. JReprod. Immunol. Microbiol.* 11(4):118-24, Roussev et al., 1995, *Am. Reprod. Immunol.* 33(2):171-175 and Thomason et al., 1995, *Am. J Reprod. Immullol.* 34(6):338-41.).

In the in vitro clinical assay, mononuclear leukocytes are isolated from women suffering from recurrent spontaneous abortion. The leukocytes are cultured, and the culture medium is removed from the leukocytes. This culture medium is then contacted with murine embryos. Toxic factors in the culture medium typically kill the murine embryos in this assay.

The mononuclear leukocytes are incubated with G-CSF prior to removal of the culture medium. The culture medium is then removed from the leukocytes and contacted with murine embryos. Survival of the murine embryos indicates or reduction of embryotoxic factors in the culture medium and thereby the effectiveness of G-CSF administration for prevention of spontaneous abortion in this in vitro model.

Example 2

G-CSF Prevents Spontaneous Abortion In A Mouse Model in Vitro

G-CSF effectively inhibits a well-known in vivo model for spontaneous abortion.

The murine mating pair CBA×DBA/2 (see e.g., Yabuki et al., 2003, *Exp. Anim.* 52(2) 159-63) results in a spontaneous abortion rate of approximately 40%. In this example, female CBA mice are treated according to the methods of the invention. They are treated with G-CSF prior to mating, at the time of mating and immediately after mating. A reduction of the rate of spontaneous abortion in mice treated with G-CSF relative to control mice indicates that G-CSF effectively prevents spontaneous abortion in this in vivo model.

Example 3

G-CSF Prevents Habitual Abortion In Vivo

Thirty-one women with habitual abortion, having more than three abortions, were recruited in the study (Scarpellini & Sbracia, 2004, *Am. J Repro. Imm.* 51(6)433-4). The cytogenetic studies, hysterosalpingography, ultrasound, endometrial biopsy, hormonal assays (estradiol, progesterone, prolactin, thyroid hormones etc.) diabetes workup and autoantibody tests (ACA, AND, AMA, SMA and anti-lupus Ab) were unremarkable. All of the women failed a previous treatment with Igs, or corticosteroid and aspirin in the former pregnancy. Sixteen women were randomly chosen and treated with filgrastim at 100 mg/day SC, which was started the sixth day after ovulation and continued through the 35th day after ovulation. The other 15 women received a placebo and progesterone.

In the group receiving filgrastim, 14 of 16 became pregnant and maintained pregnancy during the recording period. The karyotype of the fetuses was normal. In the control group, only four pregnancies occurred. hCG levels in the treated women were increased by a third over the levels observed in the control women.

All publications and patent applications in this specification are herein incorporated by reference as if each individual publication or patent application were specifically and individually indicated to be incorporated by reference in entirety. Although the foregoing invention has been described in some detail by way of illustration and example for purposes of clarity of understanding, it will be readily apparent to those of ordinary skill in the art in light of the teachings of this invention that certain changes and modifications may be made thereto departing from the spirit or scope of the invention described herein.

I claim:

1. A method for reducing the risk of preterm labor, comprising administering to a human female an effective amount of a granulocyte colony stimulating factor (G-CSF), wherein the G-CSF is administered at a dose ranging from 1 to 100 mcg (micrograms)/kg/day for a plurality of days, and wherein the human female is at risk of preterm labor.

2. The method of claim 1 wherein the G-CSF is administered at a dose ranging from 1 mcg/kg/day to 20 mcg/kg/day.

3. The method of claim 1 wherein the G-CSF is administered at a dose ranging from 1 mcg/kg/day to 10 mcg/kg/day.

4. The method of claim 1 wherein the G-CSF is filgrastim or pegfilgrastim.

5. The method of claim 1 wherein the G-CSF is administered in the second trimester of pregnancy, third trimester of pregnancy, or both.

6. The method of claim 1 wherein the G-CSF is administered before the second or third trimester of pregnancy.

7. The method of claim 1 wherein the G-CSF is administered through the end of pregnancy.

8. The method of claim 1 wherein the G-CSF is administered for the duration of pregnancy.

9. The method of claim 1 wherein the G-CSF is administered for four, three, two or one week.

10. The method of claim 1 wherein the G-CSF is administered for five, four, three, or two days.

11. The method of claim 1 wherein the G-CSF is administered about two days, about three days, about four days, about one week, about two weeks or up to about eight weeks, following signs of preterm labor.

12. The method of claim 1 wherein the G-CSF is administered parenterally, enterally, subcutaneously, percutaneously, transdermally, intradermally, intravenously, topically, by inhalation, or by implantation.

13. The method of claim 1 wherein the G-CSF is administered with another active agent.

14. The method of claim 13 wherein the other active agent is an immunosuppressive agent or an anti-inflammatory agent.

15. The method of claim 13 wherein the other active compound is vitamin D or aspirin.

16. The method of claim 13 wherein the other active compound is heparin, intravenous immunoglobulin (IVIG) or progesterone.

17. The method of claim 1 wherein the G-CSF is formulated as a composition comprising a pharmaceutically acceptable carrier or diluent.

18. The method of claim 1 wherein the G-CSF is formulated for prolonged delivery.

19. The method of claim 18 wherein the prolonged delivery results from a formulation comprising G-CSF conjugated to a water soluble polymer.

20. The method of claim 19 wherein the G-CSF conjugated to a water soluble polymer is pegfilgrastim.

21. The method of claim 18 wherein the G-CSF is formulated for prolonged delivery with a polymeric or a hydrophobic material.

22. The method of claim 18 wherein the prolonged delivery formulation comprises an inert matrix or device.

23. The method of claim 18 wherein the prolonged delivery formulation comprises an adhesive disc or patch capable of slowly releasing G-CSF for percutaneous, transdermal, or intradermal adsorption.

24. The method of claim 23 wherein the disc or patch further comprise a skin permeation enhancer.

25. The method of claim 1 wherein the human female is in the second or third trimester of pregnancy.

26. The method of claim 1 wherein the human female was a recipient of an assisted reproduction procedure.

27. The method of claim 26 wherein the assisted reproduction procedure is in vitro fertilization, artificial insemination, or gamete intrafallopian tube transfer.

28. The method of claim 1 wherein the G-CSF is administered subcutaneously.

29. A method for reducing the risk of preterm labor, comprising administering to a human female at risk of preterm labor an effective amount of a granulocyte colony stimulating factor (G-CSF), wherein the G-CSF is administered at a dose ranging from 1 to 100 mcg (micrograms)/kg/day formulated for prolonged delivery.

30. The method of claim 29 wherein the G-CSF is administered at a dose ranging from 1 mcg/kg/day to 20 mcg/kg/day.

31. The method of claim 29 wherein the G-CSF is administered at a dose ranging from 1 mcg/kg/day to 10 mcg/kg/day.

32. The method of claim 29 wherein the G-CSF is filgrastim or pegfilgrastim.

33. The method of claim 29 wherein the G-CSF is administered in the second trimester of pregnancy, third trimester of pregnancy, or both.

34. The method of claim 29 wherein the G-CSF is administered before the second or third trimester of pregnancy.

35. The method of claim 29 wherein the G-CSF is administered through the end of pregnancy.

36. The method of claim 29 wherein the G-CSF is administered for the duration of pregnancy.

37. The method of claim 29 wherein the G-CSF is administered for four, three, two or one week.

38. The method of claim 29 wherein the G-CSF is administered for five, four, three, two or one day.

39. The method of claim 29 wherein the G-CSF is administered about one day, about two days, about three days, about four days, about one week, about two weeks and up to about eight weeks, following signs of preterm labor.

40. The method of claim 29 wherein the G-CSF is administered parenterally, enterally, subcutaneously, percutaneously, transdermally, intradermally, intravenously, topically, by inhalation, or by implantation.

41. The method of claim 29 wherein the G-CSF is administered subcutaneously.

42. The method of claim 29 wherein the G-CSF is administered with another active agent.

43. The method of claim 42 wherein the other active agent is an immunosuppressive agent or an anti-inflammatory agent.

44. The method of claim 42 wherein the other active compound is vitamin D or aspirin.

45. The method of claim 42 wherein the other active compound is heparin, intravenous immunoglobulin (IVIG) or progesterone.

46. The method of claim 29 wherein the prolonged delivery formulation comprises a pharmaceutically acceptable carrier or diluent.

47. The method of claim 29 wherein the prolonged delivery formulation comprises G-CSF conjugated to a water soluble polymer.

48. The method of claim 29 wherein the G-CSF conjugated to a water soluble polymer is pegfilgrastim.

49. The method of claim 29 wherein the prolonged delivery formulation comprises a polymeric or a hydrophobic material.

50. The method of claim 29 wherein the prolonged delivery formulation comprises an inert matrix or device.

51. The method of claim 29 wherein the prolonged delivery formulation comprises an adhesive disc or patch capable of slowly releasing G-CSF for percutaneous, transdermal, or intradermal adsorption.

52. The method of claim 51 wherein the disc or patch further comprise a skin permeation enhancer.

53. The method of claim 29 wherein the human female was a recipient of an assisted reproduction procedure.

54. The method of claim 53 wherein the assisted reproduction procedure is in vitro fertilization, artificial insemination, or gamete intrafallopian tube transfer.

* * * * *

UNITED STATES PATENT AND TRADEMARK OFFICE
CERTIFICATE OF CORRECTION

| | | |
|---|---|---|
| PATENT NO. | : 8,481,488 B2 | Page 1 of 1 |
| APPLICATION NO. | : 13/458823 | |
| DATED | : July 9, 2013 | |
| INVENTOR(S) | : Darryl Carter | |

It is certified that error appears in the above-identified patent and that said Letters Patent is hereby corrected as shown below:

In the Claims:

Column 25, Line 10:
"48. The method of claim 29 wherein the G-CSF conjugated" should read, --48. The method of claim 47 wherein the G-CSF conjugated--.

Signed and Sealed this
First Day of April, 2014

Michelle K. Lee
*Deputy Director of the United States Patent and Trademark Office*